(12) United States Patent
Ponomarev

(10) Patent No.: US 9,696,139 B2
(45) Date of Patent: Jul. 4, 2017

(54) SYSTEM AND METHOD FOR IMPROVED VISUAL DETECTION OF PROTECTIVE COATINGS

(75) Inventor: Sergey G. Ponomarev, Lynnwood, WA (US)

(73) Assignee: THE BOEING COMPANY, Chicago, IL (US)

( * ) Notice: Subject to any disclaimer, the term of this patent is extended or adjusted under 35 U.S.C. 154(b) by 285 days.

(21) Appl. No.: 13/532,480

(22) Filed: Jun. 25, 2012

(65) Prior Publication Data

US 2013/0342824 A1 Dec. 26, 2013

(51) Int. Cl.
*G01B 11/06* (2006.01)
*G01N 21/84* (2006.01)

(52) U.S. Cl.
CPC ..... *G01B 11/0658* (2013.01); *G01N 21/8422* (2013.01); *G01N 2021/8427* (2013.01); *Y10T 428/31678* (2015.04)

(58) Field of Classification Search
USPC ................................................ 427/8; 356/51
See application file for complete search history.

(56) References Cited

U.S. PATENT DOCUMENTS

| | | | |
|---|---|---|---|
| 4,250,382 A | 2/1981 | Libby | |
| 4,783,166 A | 11/1988 | Stern | |
| 5,191,803 A | 3/1993 | Gamache | |
| 5,990,219 A | 11/1999 | Sakai et al. | |
| 6,060,157 A * | 5/2000 | LaPerre et al. | 428/325 |
| 6,538,725 B2 | 3/2003 | Potyrailo et al. | |
| 6,605,365 B1 | 8/2003 | Krienke et al. | |
| 6,749,777 B2 * | 6/2004 | Argoitia et al. | 252/582 |
| 7,105,834 B2 | 9/2006 | Angal et al. | |
| 7,300,695 B2 | 11/2007 | Argoitia et al. | |
| 7,811,374 B2 | 10/2010 | Osborne et al. | |
| 7,981,210 B2 | 7/2011 | Kwan et al. | |
| 7,981,529 B2 | 7/2011 | Kitamura et al. | |
| 2003/0104206 A1 | 6/2003 | Argoitia et al. | |
| 2005/0100667 A1 * | 5/2005 | Mayer et al. | 427/248.1 |

(Continued)

FOREIGN PATENT DOCUMENTS

| | | |
|---|---|---|
| JP | 2004510966 A | 4/2004 |
| WO | WO200228973 A1 | 4/2002 |
| WO | WO2007027543 A3 | 3/2007 |

OTHER PUBLICATIONS

Lunacek et al, "White-Light Interferometric Method to Measure Thickness of Thin Films", (2007), 1-7.*

(Continued)

*Primary Examiner* — Nathan T Leong
(74) *Attorney, Agent, or Firm* — Parsons Behle & Latimer

(57) ABSTRACT

The present disclosure provides a system and method for providing an improved protective coating for a substrate that may be inspected using the unaided eye or other apparatus under available light. The protective coating is mixed with an additive comprising flakes or particles that, when applied to the substrate as part of the protective coating, allow the user to empirically determine if the surface has received an adequate protective coat. The determination of whether or not any defects exist may include comparing the observed appearance of the specialty pigment particles with a comparative standard.

18 Claims, 3 Drawing Sheets

(56) References Cited

U.S. PATENT DOCUMENTS

2007/0044704 A1 3/2007 Osborne et al.
2010/0330264 A1* 12/2010 Osborne et al. ................ 427/10

OTHER PUBLICATIONS

Coatings World, Specialty Pigments Definiton found on Internet: http://www.coatingsworld.com/buyersguide/specialty-pigments/, 2010.
Standox, "The Quick Way to a Pefect Color Match," found on internet: http://www.standox.com/standox/com/en/images/colortools/THK_Quick%020Way_GB.pdf, Oct. 31, 2008.
Sherwin-Willaims, "Opti-Check (TM) Optically Activated Pigments," found on internet: http://protective.sherwin-williams.com/pdf/Opti-Check-Round-Up.pdf, Jan. 2009.
Canadian Intellectual Property Office; Office Action; Canadian Patent Application No. 2,810,197 dated Jul. 28, 2015.
European Patent Office; Extended European Search Report; European Patent Application No. 13164160.7 dated Aug. 21, 2015.
Japan Patent Office; Office Action issued in Japanese Patent Application No. 2013-131682 dated Mar. 14, 2017.

* cited by examiner

SYSTEM AND METHOD FOR IMPROVED VISUAL DETECTION OF PROTECTIVE COATINGS

FIELD

The present disclosure relates generally to a system and method for applying a protective coating to a substrate. More specifically, the present disclosure relates to additives for protective coatings, and related methods for conducting inspections of components coated with a protective coating containing said additive, thereby ensuring proper coverage. The disclosure has particular utility with respect to the application of corrosion inhibiting compounds ("CIC") in the form of a coating to aircraft components.

BACKGROUND

Various articles of commerce and general use a coating of some kind on surfaces thereof for a specific purpose, such as to prevent corrosion, to reduce abrasion, to reduce contamination or to perform a combination of the three. Discontinuities in a coating are frequently very minute and not readily visible. Since the quality and cost of the coating is dependent on the coating weight and uniformity it is desirable that a means for monitoring these characteristics be employed.

Aircraft surfaces in particular are often coated with a corrosion inhibiting compound ("CIC"), sometimes called a corrosion prevention compound, to preserve the aircraft components and structure. A typical CIC is substantially transparent, and is only apparent to the naked eye when a thick coat is applied, which appears to give a brownish tint to the substrate. But while it is important to achieve adequate coverage of designated surfaces, it may be desirable to use a thin coating to reduce excess weight.

Many techniques have been developed to enable inspection of coated surfaces to ensure adequate coverage. Some coatings employ fluorescent agents to permit inspection of the coated surface using a UV light source. However, since fluorescence is typically a fairly weak effect, high intensity UV light sources are required for reliable detection of inconsistencies in a given circumstance. In addition, many areas requiring protective coatings are not readily accessible and providing UV light in such areas may be difficult or prohibitive. Furthermore, many coated areas requiring inspection have irregular surfaces that require the UV light to be shone from various angles before a determination can be made regarding the adequacy of the coating. The cost of special lighting further disadvantages this solution.

Some current solutions employ cameras to capture images of the coated surfaces, but these systems usually suffer from some of the same limitations as those above. The camera solutions are difficult to use in certain spaces, are often unable to be used on remote surfaces, and are costly and time-consuming. As a result, there remains a need for an improved system and method for applying and inspecting a protective coating.

SUMMARY

The present disclosure provides a system and method wherein a protective coating is prepared with an additive comprising flakes or particles that, when applied to the substrate as part of the protective coating, allow the user to visually inspect the surface and empirically determine if the surface has received an adequate protective coat. The flakes or particles of the present disclosure tend to reflect light in a manner that allows the user to observe with the naked eye whether or not the coating is sufficient, even in circumstances where only minimal light is available.

The system of the present disclosure is not restricted to particular sources of light. Any available visible and/or ultraviolet light source can be used to illuminate the particles, producing reflected and emitted light, which may then be detected by unaided eyes. In turn, such a feature greatly simplifies the coating inspection.

A first aspect of the present disclosure provides a protective coating that is applied to a substrate having a plurality of specialty pigment particles embedded in the coating. The specialty pigment particles are suspended within the protective coating having a substantially homogeneous distribution. By way of example, the specialty pigment particles may comprise mica, metallic flakes, glass, marble, or any combination thereof and may be described as metal effect pigments, pearl luster pigments, interference pigments, holographic effect pigments, interference pigments, pearlescent pigments, iridescent pigments, luminescent pigments, fluorescent pigments, phosphorescent pigments, or any combination thereof.

Another aspect of the present disclosure provides a method for applying a protective coating to a substrate by mixing a predetermined amount of a protective coating formulation with a predetermined amount of a specialty pigment to form a mixture. The protective coating formulation is provided in a liquid form and the specialty pigment is provided in a particulate form. The mixture is then applied to the substrate and allowed to cure thereby forming a protective coating. A user may then observe the appearance of the specialty pigment particles embedded in the protective coating, such as the density of the specialty pigment particles or any patterns therein, to determine the presence of any inconsistencies in the coating. The user may perform the step of observing with the unaided eye or by using a digital camera device. The observing step may also include illuminating the substrate. The determination of whether or not any inconsistencies exist may include comparing the observed appearance of the specialty pigment particles with a comparative standard.

Other systems, methods, features, and advantages of the present disclosure will be or become apparent to one with skill in the art upon examination of the following drawings and detailed description. The features, functions and advantages that have been discussed can be achieved independently in various embodiments of the present invention or may be combined in yet other embodiments further details of which can be seen with reference to the following description and drawings.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure. For example, the present disclosure provides a system and method for conducting inspections of protective coatings applied to a substrate. One example of particular interest that will be discussed in detail below is the application of a corrosion inhibiting compound ("CIC") in the form of a coating to the surface of various aircraft components. The scope of the present disclosure, however, is not limited to aircraft or to CIC's, as will be apparent to those in the relevant fields of study.

Figure 1:
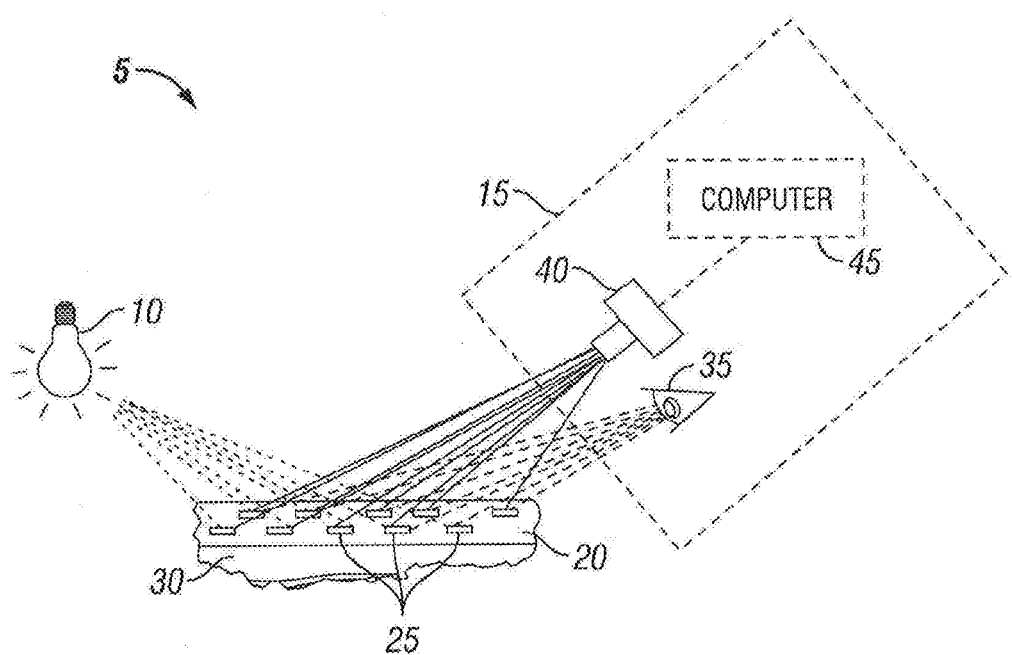
FIG. 1 is a schematic showing a system for visual inspection of protective coatings in accordance with the present disclosure.

FIG. 1 illustrates one example of a visual inspection system 5 in accordance with the present disclosure. In the illustrated example, the system 5 comprises a light source 10 and a visual inspector 15 configured to inspect a protective coating 20 applied to a substrate 30. The visual inspector 15 comprises an unaided eye 35 and/or a camera 40, which in some embodiments may be coupled to an optional computer 45. The protective coating 20 comprises a substantially homogeneous suspension of specialty pigment particles 25.

In some embodiments, the protective coating 20 comprises a formulation in a liquid form, selected from any of a number of compounds or solvents that provides the desired characteristics for a particular application. For example, the protective coating 20 may comprise one or more of a monomer or polymer composition, a petroleum-based compound, an amine, a hydrazine, or other useful compound, organic or inorganic. In some specific embodiments, the protective coating 20 comprises a petroleum-based CIC. The protective coating 20 may be derived from a formulation that has the desired viscosity and thermoplastic properties to allow the protective coating 20 to be applied simply, such as by using a sprayer, and resulting in a desired thickness.

Figure 2:
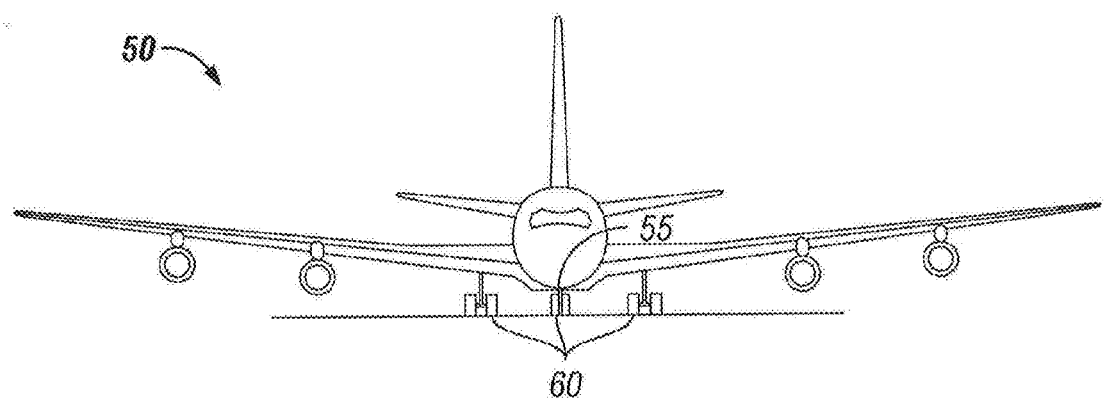
FIG. 2 illustrates a protective coating applied to a vehicle, according to one example of the present disclosure.

The substrate 30 may comprise any suitable material or surface desired to be coated. For example, in some cases, the substrate 30 comprises a surface of a vehicle 50, such as an aircraft, as shown in FIG. 2. Although an aircraft is shown as an example, those of ordinary skill in the art will appreciate that the protective coating 20 may be applied to a wide variety of other vehicles 50, such as, for example, automobiles, watercraft, trains, etc., or other desired surfaces. In the particular example illustrated in FIG. 2, the protective coating 20 comprises a CIC applied to surfaces of the vehicle 50 that are prone to corrosion, such as the lower lobe of the fuselage 55 and the landing gear 60. Depending on the application, the CIC may be reapplied periodically, such as every few years. In some embodiments, the CIC is applied as a layer having a thickness within the range of approximately 10-50 microns when dried.

Referring again to FIG. 1, the specialty pigment particles 25 may comprise any suitable particles that improve the visibility of the protective coating 20. In some embodiments, for example, the specialty pigment particles 25 may be chosen from reflective pigment particles, light emitting pigment particles, black pigment particles, or the like. Reflective pigments can be classified as effect pigments, metal effect pigments, pearl luster pigments, and interference pigments. Examples of reflective pigments include glitter-type pigments and can be selected from variety of materials such as metallic, holographic, interference, pearlescent, and iridescent pigments, glass, marble, and mica particles. In some specific embodiments, the specialty pigment particles 25 may comprise interference mica, iron oxide flakes, aluminum flakes, and the like, which in some cases may be coated with specific pigments prior to their introduction into the protective coating 20.

The specialty pigment particles 25 preferably exhibit some combination of reflectivity, diffractive, or absorbance characteristics to provide a high contrast with the light reflected by the protective coating 20 and the substrate 30. In some embodiments, for example, distinctive light contrast can be achieved with light absorbent effect pigments such as black glitter pigments. The specialty pigment particles 25 may also exhibit fluorescence when subjected to certain types of light, such as ultraviolet light. Light emitting pigments may be, for example, luminescent pigments, fluorescent pigments, and phosphorescent pigments.

The light source 10 may comprise any suitable source of visible and/or ultraviolet light, such as day light or direct sunlight, incandescent light, fluorescent light, LED light, or other types of lights. In operation, the light source 10 illuminates the protective coating 20, which reflects light for observation by a suitable visual inspector 15, such as the unaided eye 35 and/or the camera 40 and optional computer 45 shown in FIG. 1.

In some embodiments, the camera 40 and optional computer 45 comprise a self-contained, portable apparatus combined in a single housing that captures one or more digital images of the protective coating 20 under inspection. The apparatus can then detect discontinuities in the protective coating 20 and determine its uniformity and thickness based on the observed patterns of reflected light, as compared with a plurality of pre-stored images saved as comparative standards. In other examples, the camera 40 and optional computer 45 comprise separate devices that communicate with each other via a suitable link, such as a physical connector or a wireless communication link.

Figure 3:
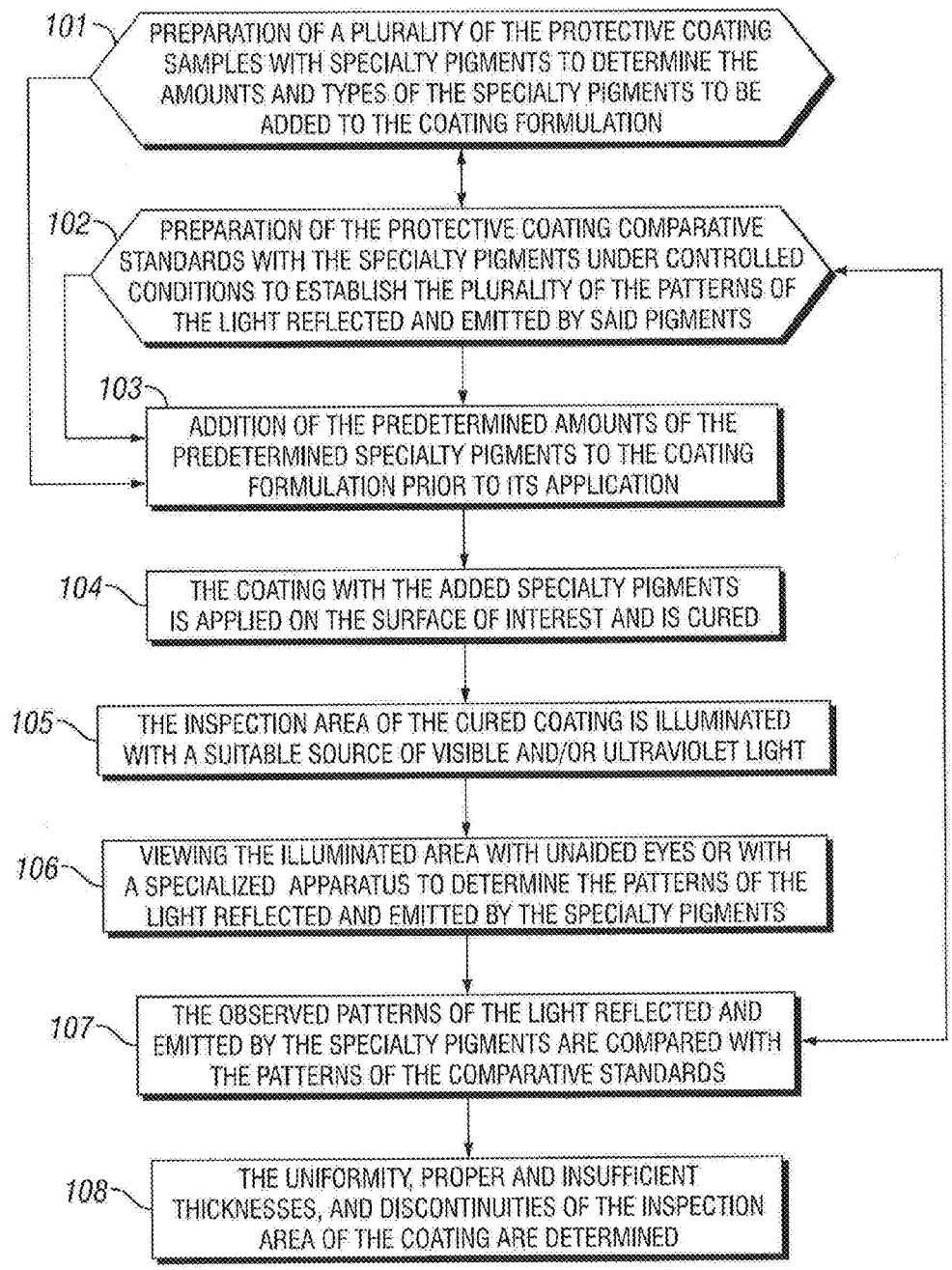
FIG. 3 is a flowchart demonstrating a method for visual inspection of protective coatings in accordance with the present disclosure.

FIG. 3 is a flowchart demonstrating one example of a method 100 for visual inspection of protective coatings 20 in accordance with the present disclosure. In the illustrated embodiment, the method 100 comprises a first step 101, in which the amounts and types of specialty pigment particles 25 to be added per unit volume to the protective coating 20 are determined prior to the formation of a mixture. This may be done, for example, by selecting a desired pigment ratio, adding a corresponding amount of specialty pigment particles 25 to a precursor of the protective coating 20, and mixing the resultant mixture until the distribution of specialty pigment particles 25 therein becomes substantially homogeneous. In some embodiments, the specialty pigment particles 25 are selected to be large enough to be noticed by the unaided eye 35 during inspection, but not larger than warranted for the application. In some cases, for example, the specialty pigment particles 25 are at least smaller than the desired thickness of the protective coating 20.

In some embodiments, the specialty pigment particles 25 are mixed in predetermined amounts and selected combinations to achieve the desired results of the visual detection of the protective coating 20. The combinations of specialty pigment particles 25 can be made to improve the visual detection of the coating uniformity, proper thickness, insufficient thickness, over-coating (excess thickness), and discontinuities such as pinholes, voids, holidays, and absence of the protective coating 20.

For example, the ratio of specialty pigment particles 25 within a certain volume of the mixture may be chosen to result in a desired distribution when the protective coating 20 is applied to a substrate 30 at a particular thickness. In some specific embodiments, for example, sufficient specialty pigment particles 25 are added to produce an expected distribution of about 10-30 specialty pigment particles 25 per square inch when the protective coating 20 is applied to a substrate 30 at a desired thickness, such as about 10-50 microns. If properly mixed and applied, any deviation from this distribution at a given location would be an indication that there is a likelihood of an inconsistency at that location. Other ranges and methods are also feasible. For example, a lower range of about 5-10 specialty pigment particles per square inch, a narrower range of about 10-20 specialty pigment particles per square inch, or an upper range of greater than about 30 specialty pigment particles per square inch may be used, depending on the application and the inspection methods that are available.

Methods for preparing a homogeneous mixture are well-known in the art. The mixture is substantially homogeneous when a portion of the volume of the mixture has a substantially similar ratio of specialty pigment particles 25 by volume as that of the entire volume of the mixture. For example, where a mixture has been prepared with a ratio of about 16 ounces of specialty pigments per gallon, and where the specialty pigments are known to have approximately 1,000 individual specialty pigment particles 25 per ounce, one could predict the approximate number of pigments within a particular volume (such as a tablespoon) using the following formula: P (pigment particles)=R (expected ratio of pigment particles per unit volume)×V (volume). In the example outlined above, one tablespoon would be expected to contain about 62.5 pigment particles 25. An acceptable range (such as within 10% of the expected number of pigment particles 25) may be determined according to the criticality of a particular application.

In some examples, the specialty pigment particles 25 are suspended in the mixture with a substantially homogeneous distribution therein, so that when the protective coating 20 is applied to the substrate 30 and dried, the visible distribution of specialty pigment particles 25 embedded in the protective coating 20 corresponds to the thickness of the protective coating 20.

Figure 4:
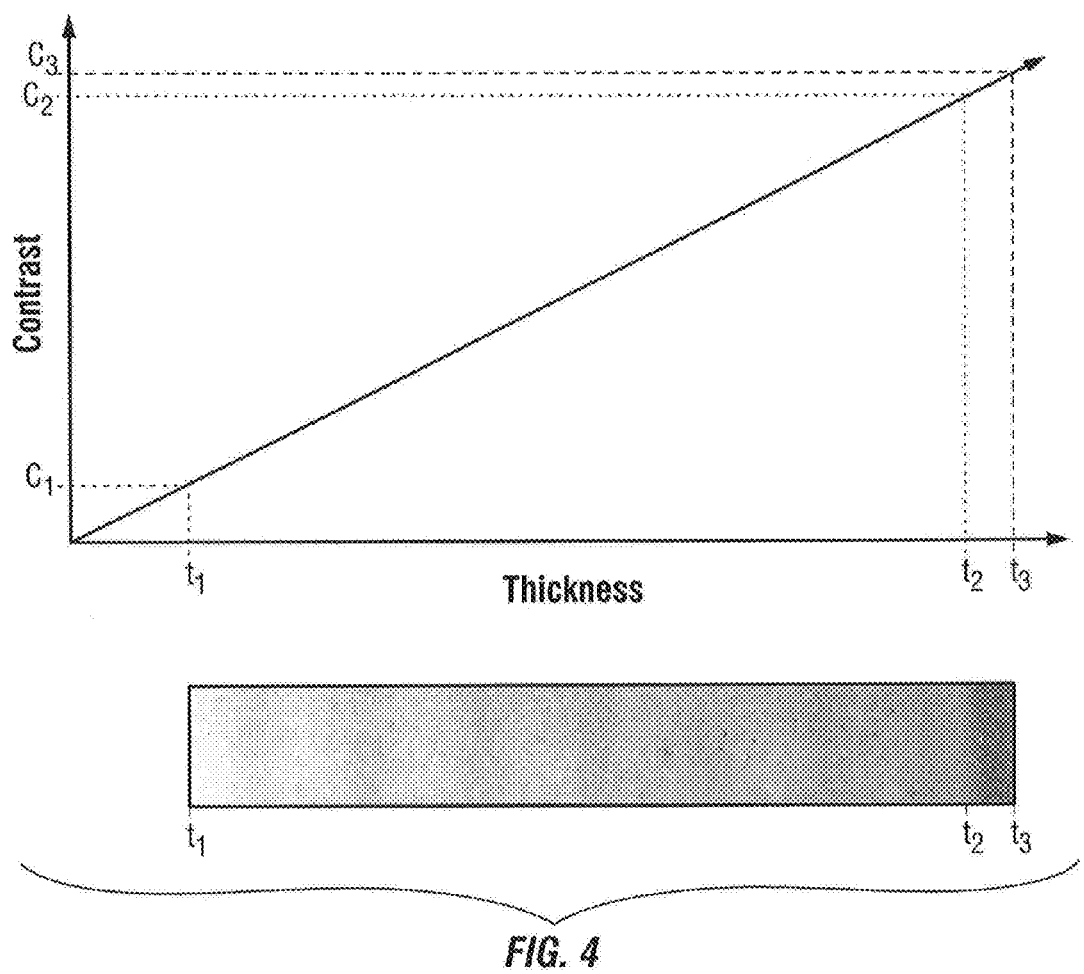
FIG. 4 provides one example of a protective coating with varying thicknesses applied to a substrate in accordance with the present disclosure.

FIG. 4 provides an example of a protective coating 20 with varying thicknesses applied to a substrate 30 in accordance with the present disclosure. As shown in FIG. 4, the observed contrast of the protective coating 20 varies directly with the thickness of the protective coating 20, as it increases along the direction of the x axis (from left to right). Thus, as the protective coating 20 becomes thicker, a corresponding increase in the density of the observed specialty pigment particles 25 occurs. Additionally, the contrast between the light reflected by the protective coating 20 and by the specialty pigment particles 25 falls within a much narrower range where the protective coating 20 is applied with the intended thickness. In the example shown in FIG. 4, for example, the thickness of the protective coating 20 is intended to fall within the range of $t_1$ to $t_2$, in which the observed light contrast falls within the range of $c_1$ to $c_2$. When overcoating occurs (e.g., when the thickness of the protective coating 20 falls within the range of $t_2$ to $t_3$), however, the protective coating 20 becomes increasingly opaque, and the observed light contrast falls within the range of $c_2$ to $c_3$. In some embodiments, $t_1$ is a thickness of about 10 microns, $t_2$ is a thickness of about 50 microns, and $t_3$ is a thickness of about 300 microns. In those embodiments, $c_1$ is a light contrast of about 10%, $c_2$ is a light contrast of about 50%, and $c_3$ is a light contrast of about 70%. In other embodiments, $t_1$-$t_3$ and $c_1$-$c_3$ may have different values, suited for a variety of desired applications.

Referring again to FIG. 3, if a test surface has a protective coating 20 of proper thickness and the specialty pigment particles 25 enable the inspection of the surface by the unaided eye, the user may determine that the initially chosen ratio is appropriate and the test surface may be used as a comparative standard for later inspections. Some examples may involve an iterative process. Once the desired ratio is known, the method 100 proceeds to a next step 102, in which comparative standards for the protective coating 20 with the specialty pigment particles 25 are prepared under controlled conditions to establish the plurality of the patterns of the light reflected and emitted by the pigment particles.

After determining the desired ratio of specialty pigment particles 25 per unit volume of the protective coating 20, and after preparing a comparative sample (if desired), in a next step 103, the mixture of the protective coating 20 with the specialty pigment particles 25 is prepared in quantities appropriate for the desired application. In a next step 104, the protective coating 20 is then applied to the substrate 30 and allowed to cure. The protective coating 20 may be applied through automated or manual processes, and may be performed using sprayers, brushes, or the like.

In a next step 105, the inspection area of the cured protective coating 20 is illuminated with a suitable light source 10. In some embodiments, the light source 10 may emit ultraviolet light, which may further enhance the ability to inspect the protective coating 20. The contrast between the light reflected by the specialty pigment particles 25 forms patterns that may be recognized by the visual inspector 15.

In a next step 106, the illuminated area of the protective coating 20 may be viewed with the visual inspector 15 to determine the patterns of the light reflected and emitted by the specialty pigment particles 25. In a step 107, the observed patterns of the light reflected and emitted by the specialty pigment particles 25 are then compared with the patterns of the comparative standards prepared separately under control conditions (see step 102).

In a final step 108, images of the protective coating 20 under inspection are compared with the comparative standards, and the uniformity, thickness, and discontinuities of the inspection area are determined. For example, the comparative standard may specify that the protective coating 20 should contain a certain number of specialty pigment particles 25 within a given area, such as each square inch. Trouble spots on a protective coating 20 under inspection may be visible to the unaided eye 35. Also, the camera 40 and optional computer 45 may identify locations that contain more or less than the expected number of specialty pigment particles 25. Other variations may be used that will allow the user to make a determination of whether or not the protective coating 20 under inspection meets a particular set of criteria.

It should be emphasized that the above-described embodiments of the present device and process are merely possible examples of implementations and merely set forth for a clear understanding of the principles of the disclosure. Many different embodiments of the disclosure described herein may be designed and/or fabricated without departing from the spirit and scope of the disclosure. All these and other such modifications and variations are intended to be included herein within the scope of this disclosure and protected by the following claims. Therefore the scope of the disclosure is not intended to be limited except as indicated in the appended claims.

The invention claimed is:

1. A protective coating for a substrate, comprising:
   a substantially transparent coating matrix; and
   a plurality of reflective particles embedded in the substantially transparent coating matrix forming a substantially transparent coating, wherein the reflective particles are arranged having a substantially homogeneous distribution within the coating matrix, wherein the plurality of reflective particles in the coating matrix produce a reflected light contrast that varies directly with a thickness of the substantially transparent coating when applied to a substrate, and wherein a concentration of the plurality of reflective particles within the coating matrix is selected to enable a thickness range of the coating matrix to be calculated based on the reflected light contrast, wherein a square inch of the coating matrix that is 10 to 50 microns thick includes 10 to 30 of the plurality of reflective particles.

2. The protective coating of claim 1, wherein the protective coating comprises a corrosion inhibiting compound.

3. The protective coating of claim 1, wherein the protective coating comprises an organic compound.

4. The protective coating of claim 1, wherein the reflective particles are formed from one or more selections from a group consisting of: mica, metallic flakes, glass, and marble.

5. The protective coating of claim 1, wherein the reflective particles comprise one or more selections from a group consisting of: metal effect pigments, pearl luster pigments, interference pigments, holographic effect pigments, interference pigments, pearlescent pigments, iridescent pigments, luminescent pigments, fluorescent pigments, and phosphorescent pigments.

6. The protective coating of claim 1, wherein the protective coating is a thin film protective coating.

7. The protective coating of claim 1, wherein the concentration of the plurality of reflective particles is further selected to correlate a range of contrast values that includes 10% to 50% to the thickness range, wherein the thickness range includes 10 microns to 50 microns.

8. A protective coating for a substrate, comprising:
   a plurality of reflective particles, substantially homogeneously distributed within a substantially transparent coating matrix forming a substantially transparent coating, wherein the plurality of reflective particles in the coating matrix produce a reflected light contrast that varies directly with a thickness of the substantially transparent coating when applied to a substrate, and wherein a concentration of the plurality of reflective particles within the coating matrix is selected to enable a thickness range of the coating matrix to be calculated based on the reflected light contrast, wherein a square inch of the coating matrix that is 10 to 50 microns thick includes 10 to 30 of the plurality of reflective particles.

9. The protective coating of claim 8, wherein the protective coating comprises a corrosion inhibiting compound.

10. The protective coating of claim 8, wherein the protective coating comprises an organic compound.

11. The protective coating of claim 8, wherein the reflective particles are selected from the group consisting of: reflective pigment particles, light emitting particles, and black pigment particles.

12. The protective coating of claim 8, wherein the reflective particles are selected from the group consisting of: mica, metallic flakes, glass, and marble.

13. The protective coating of claim 8, wherein the reflective particles are selected from the group consisting of: metal effect pigments, pearl luster pigments, interference pigments, holographic effect pigments, interference pigments, pearlescent pigments, iridescent pigments, luminescent pigments, fluorescent pigments, and phosphorescent pigments.

14. The protective coating of claim 8, wherein the protective coating is a thin film protective coating.

15. A system comprising:
   a substrate;
   a protective coating applied to the substrate, the protective coating comprising a plurality of reflective particles embedded in a substantially transparent coating matrix forming a substantially transparent coating, wherein the reflective particles are arranged having a substantially homogeneous distribution within the coating matrix, wherein the plurality of reflective particles in the coating matrix produce a reflected light contrast that varies directly with a thickness of the substantially transparent coating, and wherein a concentration of the plurality of reflective particles within the coating matrix is selected to enable a thickness range of the coating matrix to be calculated based on the reflected light contrast, wherein a square inch of the coating matrix that is 10 to 50 microns thick includes 10 to 30 of the plurality of reflective particles.

16. The system of claim 15, wherein the substrate comprises a metallic surface.

17. The system of claim 15, wherein the substrate comprises a composite surface.

18. The system of claim 15, wherein the substrate comprises the surface of an aircraft component.

* * * * *